(12) United States Patent
Menges et al.

(10) Patent No.: US 8,722,893 B2
(45) Date of Patent: *May 13, 2014

(54) PROCESS FOR MANUFACTURING 5-CHLOROMETHYL-2,3-PYRIDINE DICARBOXYLIC ACID ANHYDRIDES

(75) Inventors: Frederik Menges, Schriesheim (DE); Joachim Gebhardt, Wachenheim (DE); Michael Rack, Eppelheim (DE); Michael Keil, Freinsheim (DE); Rodney F. Klima, Quincy, IL (US); David Cortes, Quincy, IL (US); Robert Leicht, Hannibal, MO (US); Helmut Zech, Bad Duerkheim (DE); Jochen Schroeder, Lambsheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/128,779

(22) PCT Filed: Nov. 3, 2009

(86) PCT No.: PCT/EP2009/064518
§ 371 (c)(1), (2), (4) Date: May 11, 2011

(87) PCT Pub. No.: WO2010/054954
PCT Pub. Date: May 20, 2010

(65) Prior Publication Data
US 2011/0224439 A1    Sep. 15, 2011

Related U.S. Application Data

(60) Provisional application No. 61/114,223, filed on Nov. 13, 2008.

(51) Int. Cl.
*C07D 401/04* (2006.01)
*C07D 211/78* (2006.01)

(52) U.S. Cl.
USPC ........................ 546/274.1; 546/318

(58) Field of Classification Search
USPC .............................. 546/274.1, 318
See application file for complete search history.

(56) References Cited

U.S. PATENT DOCUMENTS

| | | |
|---|---|---|
| 5,026,859 A | 6/1991 | Finn |
| 5,288,866 A | 2/1994 | Strong |
| 5,334,576 A * | 8/1994 | Doehner et al. ............. 504/128 |
| 5,378,843 A | 1/1995 | Strong |
| 5,545,835 A | 8/1996 | Strong |
| 5,760,239 A | 6/1998 | Wu |

FOREIGN PATENT DOCUMENTS

| | | |
|---|---|---|
| DE | 3330604 | 3/1985 |
| EP | 0 144 595 | 6/1985 |
| EP | 0 184 027 | 6/1986 |
| EP | 0 322 616 | 7/1989 |
| EP | 0 539 676 | 5/1993 |
| EP | 0 548 532 | 6/1993 |
| EP | 0 747 360 | 12/1996 |
| EP | 0 933 362 | 8/1999 |
| JP | S62-174069 | 7/1987 |
| JP | H07-000611 | 1/1995 |
| WO | WO 2010/054952 | 5/2010 |
| WO | WO 2010/055042 | 5/2010 |
| WO | WO 2010/055139 | 5/2010 |
| WO | WO 2010/006668 | 6/2010 |

OTHER PUBLICATIONS

Zubrick, The Organic Chem Lab Survival Manual A Student's Guide to Techniques, Copyright © 1984,1988, by John Wiley & Sons, Inc.*
Tagawa, Y. et al., "Reinvestigation of nitrosation of methlypyridines and their 1-oxides and deoxygenation of 3-pyridinecarbaldehyde 1-oxide oxime", Heterocycles, (1992), pp. 1605-1612, vol. 34, No. 8.

(Continued)

*Primary Examiner* — Nizal Chandrakumar
(74) *Attorney, Agent, or Firm* — Brinks Gilson & Lione

(57) ABSTRACT

A process for manufacturing 5-chloromethyl-2,3-pyridine dicarboxylic acid anhydrides (I)

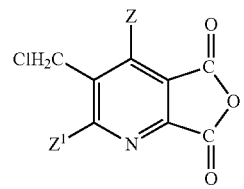

(I)

wherein
Z is hydrogen or halogen;
$Z^1$ is hydrogen, halogen, cyano or nitro;
comprising the steps of
(i) reacting a compound of formula (II),

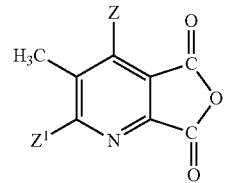
(II)

wherein the symbols have the meaning given in formula (I), with a chlorinating agent, optionally in the presence of a radical initiator in a solvent selected from halogenated hydrocarbons,
and
(ii) crystallizing the compound (I) formed in step (i) from a solvent selected from chlorobenzene, 1,2-dichlorobenzene, 1,3-dichlorobenzene, 1,4-dichlorobenzene, dichloroethane, trichloromethane, dichloromethane, toluene, xylenes, ethyl acetate, methyl tert.-butyl ether, and mixtures thereof.

Compounds (I) are useful intermediates in the synthesis of herbicidal imidazolinones.

2 Claims, No Drawings

(56) References Cited

OTHER PUBLICATIONS

International Search Report prepared in International Application No. PCT/EP2009/064518, filed Nov. 3, 2009.
International Preliminary Report on Patentability from corresponding International Application No. PCT/EP2009/064518, filed Nov. 3, 2009.
Bi, Q. et al., "Review on Synthesis of Imazamox", Modern Agrochemicals, vol. 6, No. 2, (2007), pp. 10-14.
Office Action dated Mar. 15, 2013, from corresponding U.S. Appl. No. 13/133,013.
Office Action dated Oct. 8, 2013, from corresponding U.S. Appl. No. 13/128,787.

* cited by examiner

PROCESS FOR MANUFACTURING 5-CHLOROMETHYL-2,3-PYRIDINE DICARBOXYLIC ACID ANHYDRIDES

This application is a National Stage application of International Application No. PCT/EP2009/064518 filed Nov. 3, 2009, which claims the benefit of U.S. Provisional Application No. 61/114,223, filed Nov. 13, 2008, the entire contents of which are hereby incorporated herein by reference.

The invention relates to a process for manufacturing 5-chloromethyl-2,3-pyridine dicarboxylic acid anhydrides and further conversion of these compounds to herbicidal 5-substituted-2-(2-imidazolin-2-yl)nicotinic acids, such as imazamox.

Derivatives of 2-(2-imidazolin-2-yl)nicotinic acids, like imazamox (2-[(RS)-4-isopropyl-4-methyl-5-oxo-2-imidazolin-2-yl]-5-methoxymethyl nicotinic acid),

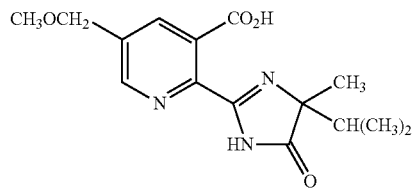

are useful selective herbicides which act as ALS-inhibitors and can be used in pre- and post-emergence applications.

Various processes for the synthesis of these compounds are known from the literature, see e.g. EP-A 0 322 616, EP-A 0 747 360, EP-A 0 933 362 or Q. Bi et al, Modern Agrochemicals 6(2)(2007) 10-14.

Although synthesis on an industrial scale is carried out by these methods there is still room for improvement, specifically in view of economical and ecological aspects, such as overall yield improvement or the avoidance of certain solvents or reagents.

EP-A 0 322 616 discloses the preparation of 5-chloromethyl-2,3-pyridine dicarboxylic acid anhydrides by chlorination of respective 5-methyl compounds in $CCl_4$. Due to the presence of unreacted starting material and dichlorination byproduct, yield and purity of the desired product are insufficient for commercial production. On the other hand, the chlorocompound is a useful intermediate in the production of herbicidal imidazolinones like imazamox.

One task of the invention is to provide an improved process for the synthesis of 5-chloromethyl-2,3-pyridine dicarboxylic acid anhydrides. A further task of the invention is to provide improved processes for manufacturing herbicidal imidazolinones, like imazamox.

It has been found that the chlorination of 5-methyl-2,3-pyridine dicarboxylic acid anhydride can be improved by using specific solvents as reaction medium and for purification of the product by (re)crystallization. It was found that only the desired mono-chlorinated products precipitate from certain solvents (or solvent mixtures). The starting material and overchlorinated products, however, stay in solution.

Accordingly, in one aspect of the invention there is provided a process for manufacturing 5-chloromethyl-2,3-pyridine dicarboxylic acid anhydrides (I),

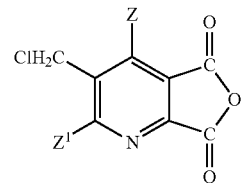

wherein
Z is hydrogen or halogen;
$Z^1$ is hydrogen, halogen, cyano or nitro;
comprising the steps of
(i) reacting a compound of formula (II),

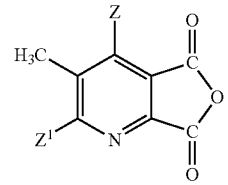

wherein the symbols have the meaning given in formula (I), with a chlorinating agent, optionally in the presence of a radical initiator in a solvent selected from halogenated hydrocarbons,
and
(ii) crystallization of the compound (I) formed in step (i) from a solvent selected from 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates (e.g. ethyl acetate, butyl acetate, methyl acetate), methyl tert.-butyl ether, diisopropylether, cyclopentyl methyl ether, and mixtures thereof.

In a further aspect of the invention there is provided a process for manufacturing an amide of formula (III),

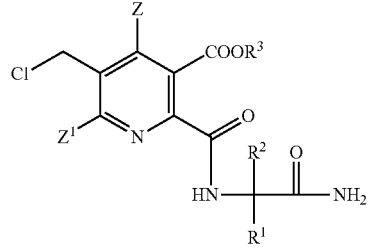

where
Z, $Z^1$ are as defined in formula (I);
$R^1$ is $C_1$-$C_4$ alkyl;
$R^2$ is $C_1$-$C_4$ alkyl, $C_3$-$C_6$ cycloalkyl or $R^1$ and $R^2$, when taken together with the atom to which they are attached, represent a $C_3$-$C_6$ cycloalkyl group optionally substituted with methyl, and
$R^3$ is hydrogen or a cation, preferably selected from the group consisting of alkali metals, alkaline earth metals, manganese, copper, iron, zinc, cobalt, lead, silver, nickel, ammonium and organic ammonium, comprising the steps of:
(i)/(ii) preparing a compound of formula (I) as described above,
and
(iii-a) reacting compound (I) with an 2-aminoalkane carboxamide (IV)

H$_2$N—CR$^1$R$^2$—CONH$_2$ (IV)

where R$^1$ and R$^2$ are as in formula (III),
or
(iii-b) reacting compound (I) with a 2-aminoalkane carbonitrile (V) (iii-b1),

H$_2$N—CR$^1$R$^2$—CN (V)

where R$^1$ and R$^2$ are as in formula (I), and (iii-b2) hydrolyzing the nitrile group to yield the respective amide (III).

In a further aspect of the invention there is provided a process for preparing a herbicidal imidazolinone compound of formula (VI),

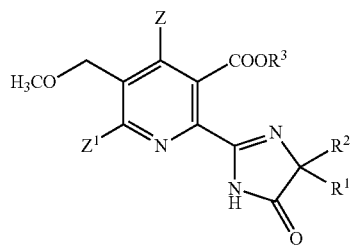

(VI)

wherein
Z, Z$^1$, R$^1$, R$^2$, R$^3$ are as defined in formula (III);
comprising the steps of:
(i)/(ii)/(iii) preparing a compound of formula (III) as described above, and
(iv) converting the compound of formula (III) into the herbicidal compound of formula (VI).

The process of the invention leads to higher yields, an improved selectivity, and higher purity for the compounds of formula (I).

Preferred are compounds of formula (I) where Z and Z$^1$ are hydrogen.

Accordingly, a particularly preferred compound of formula (I) is the compound of formula (Ia):

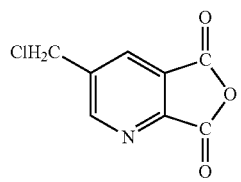

(Ia)

Compounds of formula (II) and their preparation are known, e.g. from EP-A 0 933 362.

Suitable chlorinating agents include chlorine, sulfurylchloride, N-chlorosuccinimide, and trichloroisocyanuric acid. Preferred chlorinating agents are chlorine and sulfurylchloride (SO$_2$Cl$_2$).

The molar ratio of pyridine compound (II) to chlorinating agent is generally in the range of 1:0.5-1.5, preferably 1:0.7-1.2, more preferably 1:0.8-1.1.

Suitable free-radical generators for initiating the reaction are those which decompose at the selected reaction temperature, i.e. both those which decompose by themselves and those which do so in the presence of a redox system. Examples of preferred initiators are free-radical generators, such as azo compounds and peroxides. It is also possible, however, to use redox systems, especially those based on hydroperoxides, such as cumene hydroperoxide. Light induced chlorination without addition of an initiator is also possible.

Radical initiators suitable for use in the method of the invention include 2,2'-azobisisobutyronitrile (AIBN), 2,2'-azobis(2-methylbutyronitrile), 2,2'-azobis(2,4-dimethylpentane-nitrile), 1,1'-azobis(cyclohexanecarbonitrile), organic and inorganic peroxides such as dilauroyl peroxide, hydrogen peroxide, benzoyl peroxide and the like, with 2,2'-azobisisobutyronitrile, 2,2'-azobis(2-methylbutyronitrile) and dilauroyl peroxide being preferred, and 2,2'-azobisisobutyronitrile being particularly preferred.

Preferably the initiator is added continuously over the course of the reaction.

The molar ratio of initiator to chlorinating agent is preferably in the range of 0.001-0.1:1, more preferably 0.002-0.05:1.

Organic solvents for step (i) are halogenated hydrocarbons, preferably chlorinated hydrocarbons, more preferably chlorinated aliphatic or aromatic hydrocarbons. Most preferred are solvents selected from chlorobenzene, 1,2-dichlorobenzene, 1,3-dichlorobenzene, 1,4-dichlorobenzene, 1,2-dichloroethane and tetrachloromethane, preferably 1,2-dichlorobenzene, 1,3-dichlorobenzene, 1,4-dichlorobenzene, 1,2-dichloroethane, and chlorobenzene. Chlorobenzene is particularly preferred. The term solvent as used herein includes mixtures of two or more of the above compounds. In addition the term comprises solvents that contain up to 20% by weight, preferably up to 10% by weight, in particular up to 5% by weight of further solvents which are not halogenated hydrocarbons.

The amount of organic solvent may vary to a large extent. Preferably 250 g to 1500 g, more preferably 500 g to 1000 g, of organic solvent per mol of compound (II) are employed.

In one preferred embodiment (where the chlorinating agent is a liquid) step (i) is carried out by dissolving compound (II) in the organic solvent, heating, and slowly adding a solution of the initiator in the chlorinating agent. After completion of the reaction the solvent is partly or completely distilled off, and the mixture is slowly cooled down to precipitate the product.

Alternatively the chlorinating agent can be precharged into the reaction vessel together with compound (II).

In a further preferred embodiment compound (II) and the initiator are dissolved in the solvent, and gaseous chlorine is charged to the reaction vessel or passed through the solution. After completion of the reaction the solvent is at least partly distilled off to remove excess chlorine and gaseous byproducts such as HCl. The reaction mixture is then cooled down and compound (I) is precipitated.

In a further preferred embodiment reaction (step (i)) is carried out as a continuous operation.

If chlorine is used as chlorinating agent the reaction is generally carried out at a temperature of about 0 to about 160° C., preferably about 60 to about 140° C., particularly preferred about 80 to about 120° C.

If a liquid chlorinating agent is used, in particular sulfurylchloride, the reaction is generally carried out at a temperature of about 0 to about 140° C., preferably about 50 to about 120° C., particularly preferred about 70 to about 90° C.

The reaction may be carried out under atmospheric pressure or under elevated pressure of up to 6 bar, preferably up to 2 bar. Elevated pressure is preferred if chlorine is used as chlorinating agent.

The reaction time (for step (i)) differs with the reaction parameters but is generally between 5 min and 300 h. In case of a continuous reaction the residence time in the reaction vessel is preferably in the range of 2 to 10 minutes, in particular about 5 minutes.

In step (ii) of the reaction compound (I) is crystallized from a solvent selected from chlorobenzene, 1,2-dichlorobenzene, 1,3-dichlorobenzene, 1,4-dichlorobenzene, 1,2-dichloroethane, trichloromethane, toluene, xylenes, mesitylenes, ethyl acetate, butyl acetate, methyl acetate, methyl tert.-butyl ether, diisopropyl ether, cyclohexyl methyl ether, and mixtures thereof.

The term solvent as used herein includes solvent mixtures.

Chlorobenzene and the dichlorobenzenes are preferred, chlorobenzene is particularly preferred.

It is possible that the solvent used for crystallization comprised up to 90% by weight, preferably from 10 to 80% by weight, in particular 20 to 60% by weight of an anti-solvent, i.e. a liquid in which the compound of formula (I) is essentially insoluble, such as aliphatic hydrocarbons, like n-hexane, iso-hexanes, or cyclohexane.

Crystallization is generally carried out at a temperature in the range from about −40 to 30° C., preferably about 0 to about 20° C. The concentration of compound (I) in the solvent from which it is crystallized is generally in the range of from 5 to 60% by weight, preferably 10 to 50% by weight.

Crystallization can be carried out by standard methods, e.g. by cooling of a saturated solution of compound (I), by seeding with pure compound (I), by adding an anti-solvent, or by a combination of these methods.

According to the invention compound (I) must be at least once crystallized from one of the above listed solvents or a mixture of two or more of these solvents.

In a preferred embodiment of the invention the chlorination of step (i) is carried out in a solvent which can be used for the crystallization of step (ii). Preferably compound (I) is then crystallized from the reaction mixture after the completion of step (i).

Optionally the original solvent may be partially (or completely) distilled off, and it is also possible to add further solvent, e.g. to compensate for solvent that was distilled off.

It is further preferred to recrystallize compound (I) once or more, preferably once, to improve the purity of the product. Recrystallization is usually carried out in the same solvent as the initial solvent, but of course it is also possible to use a different solvent or solvent mixture from the listed group.

The mother liquor of a recrystallization is preferably recycled to the first crystallization step to minimise yield losses.

In a further preferred embodiment of the invention the chlorination of step (i) is carried out in a solvent which is different from the solvents used for the crystallization of step (ii). In this embodiment the solvent of step (i) is removed, and raw compound (I) is dissolved in a solvent of step (ii) and crystallized. One or more re-crystallization steps with the same or different solvents are or course possible, and mother liquor can be recycled as stated above.

It is preferred that the same solvent is used in step (i) and (ii), in particular chlorobenzene or dichlorobenzene.

The purity of compound (I) after (re)crystallization, determined by HPLC (after quench of the analyt with methanol), is preferably at least 95%, more preferably at least 98%.

Isolation of compound (I) after (re)crystallization can be carried out by standard methods, e.g. by filtration, washing with a suitable solvent and drying.

The compounds of formula (I) are valuable intermediates in organic synthesis. They are especially useful for conversion to amido compounds (III) and further to herbicidal imidazolinone compounds (VI).

In one aspect of the invention there is provided a process for producing compounds of formula (III) comprising the steps of:
(i)/(ii) preparing a compound of formula (I) as described above,
(iii-a) reacting compound (I) with an 2-aminoalkane carboxamide (IV)

$$H_2N-CR^1R^2-CONH_2 \quad (IV)$$

where $R^1$ and $R^2$ are as in formula (III),
or
(iii-b) reacting compound (I) with a 2-aminoalkane carbonitrile (V) (iii-b1),

$$H_2N-CR^1R^2-CN \quad (VI)$$

where $R^1$ and $R^2$ are as in formula (I), and (iii-b2) hydrolyzing the nitrile group to yield the respective amide (III).

In one embodiment step (iii-a) can be carried out in analogy to the procedure disclosed in example 10 of EP-A 0 322 616. Compound (I), a substituted 2-aminoalkane carboxamide (IV) and a tertiary amine, preferably triethylamine are reacted in a polar aprotic solvent, such as acetonitrile, to yield an ammonium salt (III), which can be acidified to an acid (III).

In another preferred embodiment compound (I) is reacted with a 2-aminoalkane carbonitrile (V) (step iii-b1) to form a 2-carbamoyl-nicotinic acid (VII)

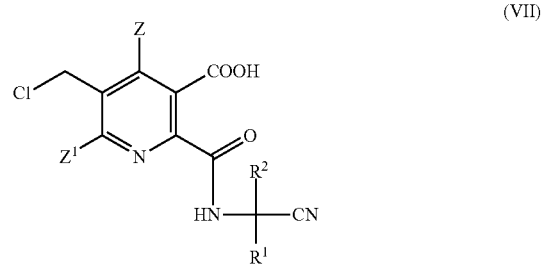

where Z, $Z^1$, $R^1$ and $R^2$ are defined as in formula (III), which is further hydrolyzed (step (iii-b2)) to yield the amido compound (III).

In a preferred embodiment, compound (Ia) is reacted with preferred 1-aminoalkane carbonitrile (Va) to form preferred carbonitrile compound (VIIa):

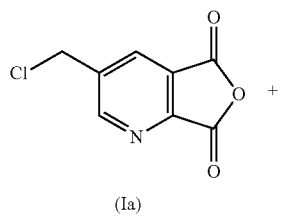

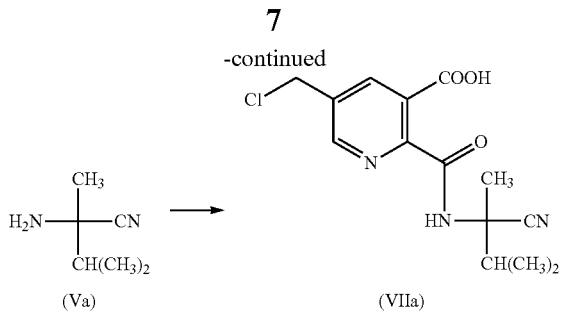

Aminonitriles (V) are commercially available or can be prepared by methods known in the art. Generally 0.8 to 1.2 equivalents aminonitrile (V) per equivalent of compound (I) are used, preferably 0.95 to 1.1.

The reaction is carried out in a solvent, which is preferably selected from aromatic hydrocarbons, preferably toluene, mesitylenes, chlorinated aromatic hydrocarbons, such as chlorobenzene, dichlorobenzene, chlorinated hydrocarbons, such as 1,2-dichloroethane, dichloromethane, acetic acid, and mixtures thereof.

If acetic acid is not used as the main solvent, addition of 0.5 to 4 equivalents, preferably 1 to 3 equivalents (based on compound (I)), is advantageous. Further advantageous additives that improve the selectivity of the ring-opening reaction (2 versus 3 position) are listed in U.S. Pat. No. 4,562,257, and comprise pyridine, 4-picoline, 2-picoline and quinoline.

The reaction is generally carried out at a temperature range of from about 40 to about 120° C., preferably of from about 60 to about 100° C. The reaction time is generally from about 1 to about 3 h.

In a preferred embodiment compound (I) is dissolved in the solvent and brought to the reaction temperature, and aminonitrile (V) is gradually added. After completion of the reaction and cooling, nitrile compound (VII) can be isolated by standard methods.

In a preferred embodiment, however, compound (VII) is not isolated but the reaction mixture is directly used in the following hydrolyzation step of the nitrile, e.g.

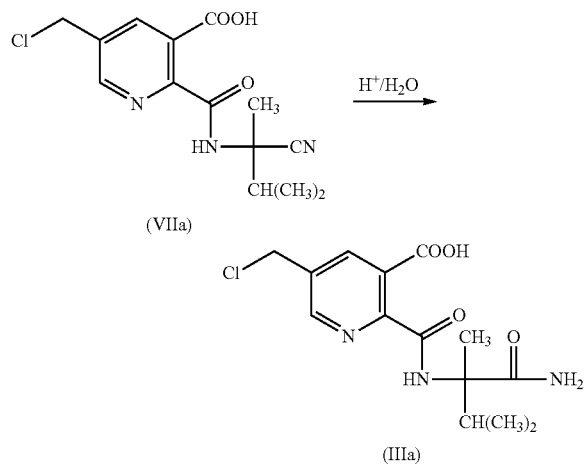

In a typical procedure a slight excess (e.g. 1.1 to 1.5 equivalents based on (VII)) of a strong mineral acid, preferably sulfuric acid (preferably in a concentration of 30 to 98%) and water (e.g. 2 to 10 equivalents) are added at a temperature which is generally in the range of about 30 to 120° C., preferably 50 to 90° C. The mixture is further stirred until complete conversion. The reaction time is generally from 1 to 8 h, preferably 1 to 5 h.

Workup and isolation can be achieved by standard methods, such as precipitation from an aqueous solution (e.g. as its ammonium salt). In a preferred embodiment the reaction mixture is directly used in the following reaction step.

In a further process of the invention an herbicidal imidazolinone compound (VI) is prepared by a process comprising the steps of (i)/(ii)/(iii-a or iii-b) preparing an amido compound of formula (III) as described above; and (iv) reacting compound (III) with $CH_3OM$ or $MOH/CH_3OH$ (where M is an alkali metal cation, preferably Na or K) followed by acidification to form the herbicidal imidazolinone (VI).

In one alternative of step (iv) amido compound (III), preferably in the form of an ammonium salt ($R^3$ is $HNR_3$), is reacted with an alkali metal methoxide, preferably $NaOCH_3$ in methanol in analogy to example 11 of EP 0 322 616. The resulting suspension is held at reflux until complete conversion. After cooling the mixture is acidified to obtain compound (III) either as the ammonium salt (acidification to a pH of about 4) or the free acid (acidification to pH≤2).

In a further preferred embodiment, compound (III), preferably the reaction mixture from step (iii), is reacted with methanol (generally 2 to 100 equivalents based on (III)) in the presence of an aqueous base (generally 3 to 100 equivalents based on (III)), the base being preferably selected from MOH and $MOCH_3$, where M is an alkali metal cation, preferably Na or K, particularly Na.

The reaction is carried out at a temperature in the range of from 20 to 120° C., preferably 40 to 90° C. The reaction can be carried out at atmospheric pressure or at elevated pressure, preferably the pressure forming at the desired reaction temperature. The reaction time is generally from 1 to 8 h, preferably from 1 to 5 h.

Isolation of product (VI) can be achieved by standard methods. In a preferred embodiment water is added and organic solvents are distilled off. The residue can be taken up in water and acidified, whereupon compound (VI) precipitates. After filtration the crude product can be further purified, e.g. by stirring with water or recrystallization.

In a further embodiment of the invention there is provided a process for preparing herbicidal imidazolinones of formula (VI) comprising the steps of (i)/(ii)/(iii-b1) preparing a carbonitrile (V) as described above and (iv) reacting compound (V) with a base selected from MOH and $MOCH_3$, where M is an alkali metal cation, and (aqueous) $H_2O_2$ in methanol, optionally followed by acidification.

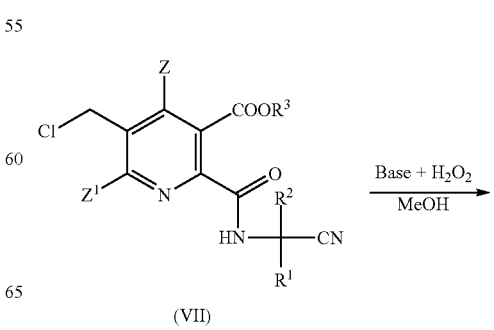

-continued

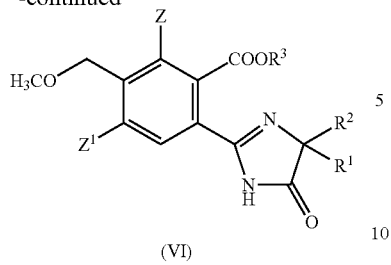

(VI)

The reaction can be carried out in analogy to the procedures described in EP-A 0 144 595.

In a further embodiment of the invention there is provided a process for preparing a compound of formula (VIII),

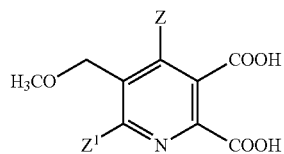

(VIII)

where Z, $Z^1$ are as in formula (I),
comprising the steps of
(i)/(ii) preparing a compound of formula (I) as described above, and
(iii) reacting compound (I) methanol in the presence of MOH or $MOCH_3$, where M is an alkali metal cation.

In a preferred embodiment (I) is dissolved in methanol (generally 2 to 100 equivalents based on (I)), and base is added (generally 3 to 100 equivalents). In a preferred embodiment water is added, preferably 5 to 200% by weight based on the base. The base is preferably selected from NaOH, KOH, $NaOCH_3$ and $KOCH_3$, NaOH, particularly as a 50% by weight aqueous solution, is especially preferred.

The reaction temperature is generally in the range of from about 20 to about 120° C., preferably about 40 to about 90° C. The reaction is generally carried out at ambient pressure or elevated pressure. The reaction time is generally from 1 to 8 h, preferably from 1 to 5 h.

Workup and isolation of compound (VIII) can be achieved by standard measures. Compound (VIII) can be treated with a dehydrating agent, such as acetic anhydride or $SO_2Cl_2$, to form the anhydride (IX),

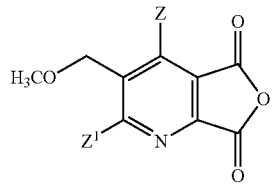

(IX)

Anhydride (IX) can be converted to herbicidal imidazolinones (VI) in analogy to the conversion of compound (I). Preparation of compounds (VI) by a respective process is a further object of the invention.

According to this embodiment of the invention a process for preparing a herbicidal imidazolinone compound of formula (VI),

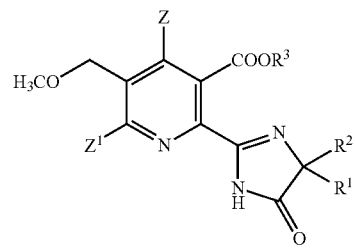

(VI)

wherein
Z, $Z^1$, $R^1$, $R^2$, $R^3$ are as defined in formula (III), is provided, comprising the steps of:
(i)/(ii) preparing a compound of formula (I) as described above,
(iii) reacting compound (I) in methanol with MOH or $MOCH_3$, where M is an alkali metal cation, followed by acidification, to form compound (VIII)

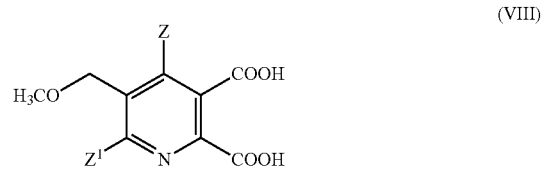

(VIII)

where Z, $Z^1$ are as in formula (I),
(iv) treating compound (VIII) with a dehydrating agent to form anhydride (IX),

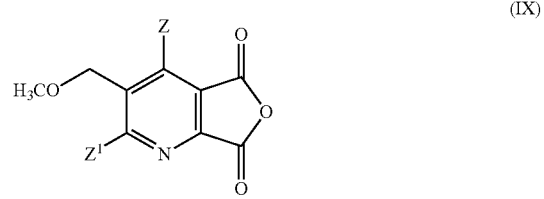

(IX)

where Z, $Z^1$ are as in formula (III), and either
(v-a1) reacting anhydride (IX) with aminonitrile (V),

$H_2N$—$CR^1R^2$—CN    (V)

where $R^1$ and $R^2$ are as in formula (VI),
to obtain nitrile compound (X),

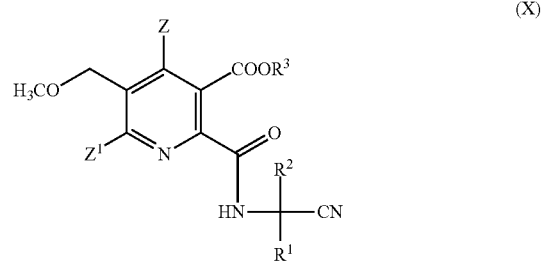

(X)

(v-a2) hydrolyzing the nitrile group in compound (X) to obtain amide (XI),

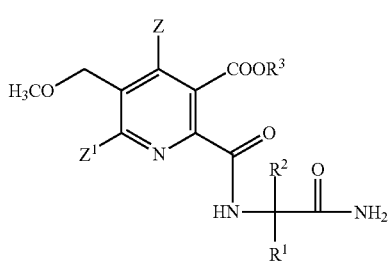

(XI)

or (v-b) reacting anhydride (IX) with an amino carboxamide (IV), $$H_2N-CR^1R^2-CONH_2 \quad (IV)$$

where $R^1$ and $R^2$ are as in formula (VI), to obtain amide (XI), and (vi) condensation of amide (XI) to yield a herbicidal imidazolinone (VI).

The invention is illustrated by the following examples without limiting it thereby.

EXAMPLE 1

Synthesis of 5-chloromethyl-2,3-pyridine dicarboxylic acid anhydride (Ia)

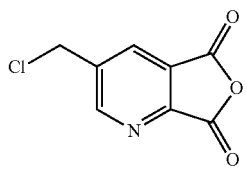

(Ia)

106.8 g (0.65 mol) of 5-methyl-2,3-pyridine dicarboxylic acid anhydride were dissolved in 427 g chlorobenzene and heated up to 85° C. A solution of 0.64 g (0.004 mol) AIBN in 99.0 g (0.66 mol) $SO_2Cl_2$ was added during 45 min. The mixture was stirred for additional 90 min at 85° C. Chlorobenzene was partly distilled off and the solution was cooled to 10° C. via 10 h ramp. The precipitate was filtered off and washed with chlorobenzene/hexane.

Yield: 85.0 g (0.40 mmol, 60%) of which 58.1 g (0.27 mmol) could be isolated after precipitation.

In all examples the solvents for steps (i) and (ii) were identical, i.e. compound (Ia) was crystallized from the reaction medium.

EXAMPLE 10

Synthesis of Imazamox (VIa)

(a) Synthesis of Carbonitrile (Va)

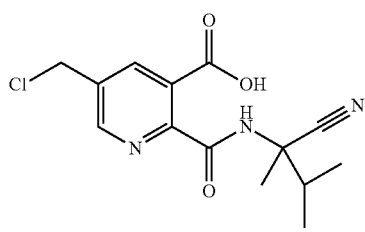 [SMILES: CC(C)C(C)(C#N)NC(=O)c1ncc(CCl)cc1C(=O)O]

9.6 g (48 mmol) anhydride (Ia), 40.0 g (435 mmol) toluene and 6.7 g (112 mmol) acetic acid were charged to a reactor and heated up to 69° C. 7.2 g (51 mmol) α-amino-1,2-dimethyl butyronitrile (Va) were added over 25 min at a temperature between 72° C. and 76° C. The mixture was stirred for additional 90 min at 75° C. After cooling the mixture was directly used in the next stage.

(b) Synthesis of 2-[(1-carbamoyl-1,2-dimethylpropyl)carbamoyl]-5-chloromethyl nicotinic acid (IIIa)

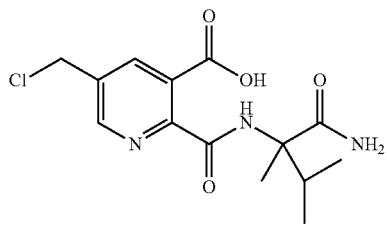 [SMILES: CC(C)C(C)(NC(=O)c1ncc(CCl)cc1C(=O)O)C(N)=O]

To 14.9 g (48 mmol) nitirile (Va) (from stage (a)), 6.0 g (59 mmol) sulfuric acid (98%) was added at 69° C. to 80° C.

TABLE 1

Synthesis of 5-chloromethyl-2,3-pyridine dicarboxylic acid anhydride (Ia)

| Example no. | Chlorinating Agent | Equivalents of chlorinating agent | Solvent (steps (i) and (ii)) | Reaction temperature [° C.] | Initiator | % Yield (by HPLC) |
|---|---|---|---|---|---|---|
| 1 | $SO_2Cl_2$ | 1.01 | MCB | 85 | AIBN | 60 |
| 2 | $SO_2Cl_2$ | 1.5 | dichloroethane | 85 | AIBN | 23 |
| 3 | $SO_2Cl_2$ | 1.5 | dichlorobenzene | 85 | AIBN | 61 |
| Comp. Ex 1 | $SO_2Cl_2$ | 12 | $CCl_4$ | 65 | AIBN | 20* |
| 4 | $Cl_2$ | 1.5 | MCB | 111 | AIBN | 56 |
| 5 | $Cl_2$ | 2.04 | MCB | 109 | ACHBN | 58 |
| 6 | $SO_2Cl_2$ | 2.13 | MCB | 110 | $(tBuO)_2$ | 29 |
| 7 | $SO_2Cl_2$ | 2.12 | MCB | 120 | TBPB | 40 |
| 8 | $SO_2Cl_2$ | 2.11 | MCB | 110 | dilauryl-peroxide | 47 |
| 9 | $SO_2Cl_2$ | 2.2 | MCB | 110 | DBPO | 40 |

MCB: Monochlorobenzene, AIBN: Azobisisobutyronitrile, ACHBN: 2,2-Azobiscyclohexanecarbonitrile, TBPB: tert.-butyl(peroxy benzonate, DBPO: dibenzoyl peroxide
*contains about 10% starting material and 10% dichloromethyl byproduct.

within 5 min. 4.1 g (228 mmol) water was added at 70° C. to 78° C. and stirring continued at 69° C. for 5 h. The emerging product forms a toluene insoluble oil. The reaction mixture was used without workup in the following stage.

(c) Synthesis of Imazamox

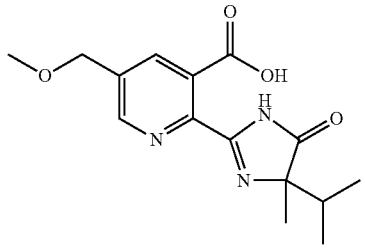 [SMILES: COCc1cnc(C2=NC(C)(C(C)C)C(=O)N2)c(C(=O)O)c1]

To 15.7 g (48 mmol) amido compound (IIIa) (reaction mixture from stage (b)) 94 g (2.94 mol) methanol was added at 65° C. and subsequently 42 g (525 mmol) NaOH (50% in water). The solution turned into a suspension, and stirring was continued for additional 90 min.

80 g water was added and solvents were removed at 50° C. and 80-8 mbar. Residue was dissolved in water and the basic solution acidified with 29 g sulfuric acid (98%). Imazamox precipitated from pH 4 on. The suspension was filtered at room temperature and washed with 100 ml water.

Yield: 16.5 g (82% pure, 44 mmol, 92%)

Purity was enhanced to >95% (HPLC) by stirring the crude product with water.

EXAMPLE 11

Synthesis of 5-methoxymethyl-2,3-pyridinedicarboxylic acid (VIIIa)

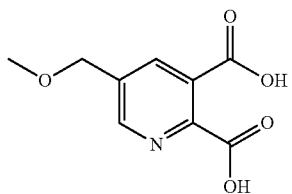

7.0 g (35 mmol) 5-chloromethyl-2,3-pyridinedicarboxylic acid anhydride were dissolved in 165 g (5.16 mol) methanol at room temperature, causing formation of monoesters. 14 g (350 mmol) NaOH (50% in water) were slowly added whereupon the temperature rose to 50° C. and carboxylate started to precipitate. Stirring was continued for additional 5 hrs at 65° C.

The solvents were then removed in vacuo, and the solid residue was dissolved in 53 g water and acidified with 19 g sulfuric acid (98%) up to pH=1.5. The aqueous solution was extracted three times with 90 g THF at 40° C. and the combined organic phases were concentrated to dryness.

Yield: 7.4 g (32 mmol, 90%)

The invention claimed is:

1. A process for preparing a compound of formula (VI),

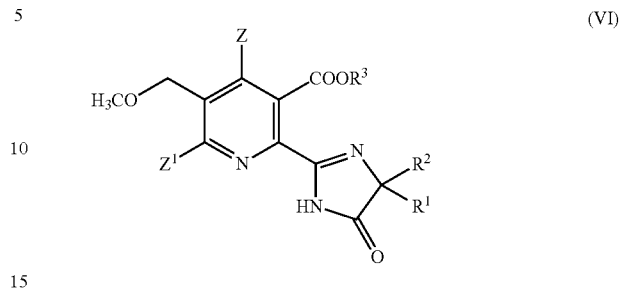

wherein

Z is hydrogen or halogen;

$Z^1$ is hydrogen, halogen, cyano or nitro;

$R^1$ is $C_1$-$C_4$ alkyl;

$R^2$ is $C_1$-$C_4$ alkyl, $C_3$-$C_6$ cycloalkyl or $R^1$ and $R^2$, when taken together with the atom to which they are attached, represent a $C_3$-$C_6$ cycloalkyl group optionally substituted with methyl, and $R^3$ is hydrogen or a cation, comprising the steps of:

(i) reacting a compound of formula (II),

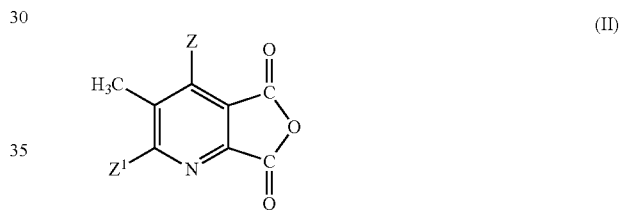

with a chlorinating agent, optionally in the presence of a radical initiator in a solvent selected from halogenated hydrocarbons, to obtain a compound of formula (I)

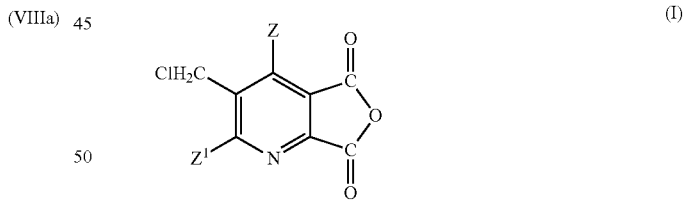

wherein

Z is hydrogen or halogen;

$Z^1$ is hydrogen, halogen, cyano or nitro;

(ii) crystallising the compound of formula (I) formed in step (i) from a solvent selected from 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates, methyl tert.-butyl ether, diisopropylether, cyclopentyl methyl ether, and mixtures thereof;

(iii) reacting compound (I) in methanol with MOH or $MOCH_3$, where M is an alkali metal cation, followed by acidification, to form compound (VIII)

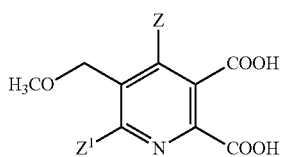
(VIII)

(iv) treating compound (VIII) with a dehydrating agent to form anhydride (IX),

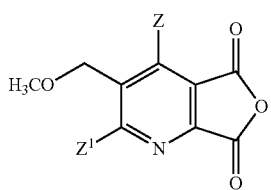
(IX)

and either (v-a1) reacting anhydride (IX) with aminonitrile (V),

$H_2N—CR^1R^2—CN$ (V)

to obtain nitrile compound (X),

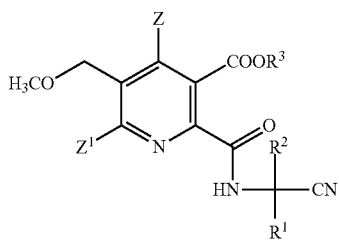
(X)

(v-a2) hydrolyzing the nitrile group in compound (X) to obtain amide (XI),

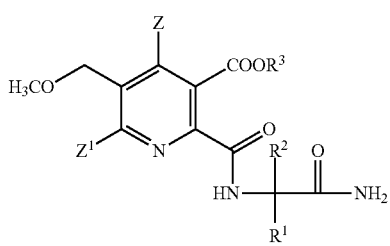
(XI)

or (v-b) reacting anhydride (IX) with an amino carboxamide (IV)

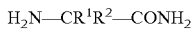
$H_2N—CR^1R^2—CONH_2$ (IV)

to obtain amide (XI), and (vi) condensing of amide (XI) to yield the compound of formula (VI).

2. A process for preparing a compound of formula (VI),

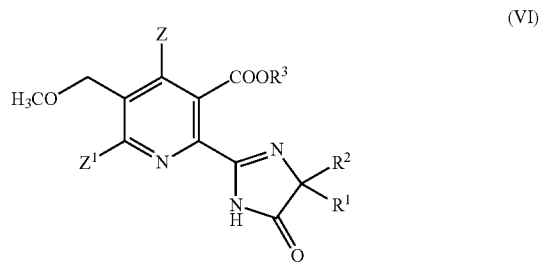
(VI)

wherein

Z is hydrogen or halogen;

$Z^1$ is hydrogen, halogen, cyano or nitro;

$R^1$ is $C_1$-$C_4$ alkyl;

$R^2$ is $C_1$-$C_4$ alkyl, $C_3$-$C_6$ cycloalkyl or $R^1$ and $R^2$, when taken together with the atom to which they are attached, represent a $C_3$-$C_6$ cycloalkyl group optionally substituted with methyl, and $R^3$ is hydrogen or a cation, comprising the steps of:

(i) reacting a compound of formula (II),

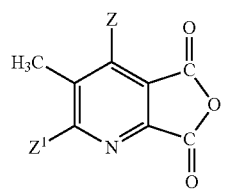
(II)

with a chlorinating agent, optionally in the presence of a radical initiator in a solvent selected from halogenated hydrocarbons, to obtain a compound of formula (I)

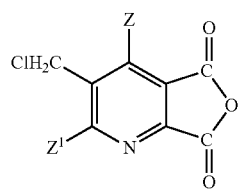
(I)

wherein

Z is hydrogen or halogen;

$Z^1$ is hydrogen, halogen, cyano or nitro;

(ii) crystallising the compound of formula (I) formed in step (i) from a solvent selected from 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates, methyl tert.-butyl ether, diisopropylether, cyclopentyl methyl ether, and mixtures thereof;

(iii) reacting compound (I) with a 2-aminoalkane carbonitrile (V),

$H_2N—CR^1R^2—CN$ (V)

to obtain nitrile (VII)
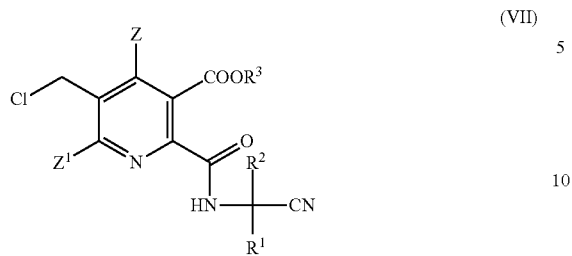
(VII)
and
(iv) reacting nitrile (VII) with (a) a base selected from MOH and MOCH$_3$, where M is an alkali metal cation, and (b) aqueous H$_2$O$_2$, in methanol, optionally followed by acidification.
* * * * *